United States Patent [19]

Rall

[11] Patent Number: 4,654,125

[45] Date of Patent: Mar. 31, 1987

[54] METHOD AND APPARATUS FOR ELECTROCHEMICAL DETECTION

[76] Inventor: Gerhard G. Rall, Baaderstrasse 55, D-8000 Munchen 5, Fed. Rep. of Germany

[21] Appl. No.: 584,806

[22] Filed: Feb. 29, 1984

[30] Foreign Application Priority Data

Mar. 1, 1983 [DE]  Fed. Rep. of Germany ....... 3307154

[51] Int. Cl.[4] ............................................. G01N 27/46
[52] U.S. Cl. .................................... 204/1 T; 204/400; 204/406; 204/412
[58] Field of Search ......................... 204/400, 406, 412

[56] References Cited

U.S. PATENT DOCUMENTS

| | | | |
|---|---|---|---|
| 3,649,504 | 3/1972 | Evans et al. | 204/412 |
| 3,709,796 | 1/1973 | King et al. | 204/412 |
| 4,326,927 | 4/1982 | Stetter et al. | 204/406 |
| 4,426,621 | 1/1984 | Galwey et al. | 204/412 |
| 4,498,039 | 2/1985 | Galwey et al. | 204/406 |

Primary Examiner—T. Tung
Attorney, Agent, or Firm—Arnold, White & Durkee

[57] ABSTRACT

A method and an apparatus for electrochemical detection of solutions containing substances to be analyzed, by means of an electrochemical detector comprising a detector cell which includes a working electrode in contact with the solution flowing through a solution flow space of the detector cell, a measuring electrode for measuring the electrolyte potential, and an auxiliary electrode for applying a potential to the electrolyte. A potential difference required for the electrolysis is generated between the electrolyte and the working electrode by means of the auxiliary electrode. The electrolysis current generated at the working electrode is taken off as an analysis measurement value. In doing so, the instantaneous electric potential value of the electrolyte in the local region of the working electrode is measured and the working electrode potential is controlled as a function of the measured instantaneous potential value.

27 Claims, 5 Drawing Figures

METHOD AND APPARATUS FOR ELECTROCHEMICAL DETECTION

BACKGROUND OF THE INVENTION

The present invention relates to a method and an apparatus for electrochemical detection and more particularly to a method and an apparatus for electrochemical detection of solutions containing at least one substance to be analyzed by means of an electrochemical detector. An electrochemical detector may have a detector cell comprising an inlet and an outlet for an electrolytic solution to be analyzed. A working electrode is in contact with the solution which flows through a solution flow space. A counter-electrode arrangement is provided by means of which an electric potential with respect to the working electrode can be impressed on the solution. The foregoing potential is capable of effecting the electrolysis of the substances in the solution which are to be analyzed at the working electrode.

An important field of use of electrochemical detection and electrochemical detectors, respectively, is the field of liquid chromatography. In this method of analysis the substance to be analyzed is added to a carrier liquid which is supplied by a pump, and the resulting solution is passed onto an analytical column. This column has a retention effect. This means that different substances of the test mixture in the solution are retained on the column for different amounts of time. The individual substances of the test mixture then arrive successively with respect to time at the exit of the column and may thus be analyzed individually.

The analysis may be performed by means of an electrochemical detector comprising a detector cell having the initially indicated features. Preferably, the solution flow space of this detector cell is designed such that the electrolytic solution flowing therethrough assumes the shape of a thin-layer. An example of a chemical detector cell of this type is shown in FIG. 1 which is taken from the publication "Detectors for Trace Organic Analysis by Liquid Chromatography: Principles and Applications," from Vo. 2 ADV. ANAL. and CLINIC. CHEM., PLENUM, NEW YORK, '78 and is hereby incorporated by reference. The electrolytic solution coming from the column is passed through a plastic tube to an inlet, flows through a thin-layer solution flow space, into which a working electrode extends, and leaves the detector cell through an outlet. From there the electrolytic solution flows through an additional plastic tube into a housing containing a potential measuring electrode (usually known as "reference electrode") by means of which the electric potential of the electrolytic solution is measured.

The electrolytic solution flows from this housing through a discharge line to a discharge means for the electrolytic solution. A part of the discharge line is formed by a short metal tube piece which is used as an auxiliary electrode via which a potential is applied to the electrolytic solution. The auxiliary electrode is necessary since the usual measuring electrodes are not current-resistant. The current which flows off via the working electrode due to an oxidation or reduction of the electrolytic solution is therefore supplied via the auxiliary electrode. As stated in the above-mentioned publication, the potential difference between the electrolyte and the working electrode, which is necessary for ionizing the electrolytic solution, is brought about by maintaining the working electrode at ground potential and by bringing the electrolyte to the required potential difference with respect to the working electrode by means of the auxiliary electrode. For this purpose, the electrolyte potential is measured by means of the measuring electrode and the potential of the auxiliary electrode is controlled with the aid of this measured value such that there is the desired potential difference between the electrolyte and the working electrode.

The current generated at the working electrode during the oxidation or reduction may be converted to a proportional voltage which, in turn, may be applied to the input of a measurement value recorder.

This recorder draws a chromatogram which shows some basic signal value (usually also called a "base line") and peaks (sometimes referred to as measurement signal peaks) standing out therefrom, the position of which on the time axis of the chromatogram depends on the type of the substances in the electrolytic solution that are to be analyzed and the height of which depends on the concentration of the substances to be analyzed. A noise and interference voltage is superimposed on the basic signal value, and the amplitude of that voltage creates a resolution limitation for the chromatogram. Thus, great efforts are made in order to keep the noise component of the basic value signal as low as possible, so as to be able to analyze substances in very small amounts.

It is known from the article "Optimierung des Signal/Rausch-Verhaltnisses bei der elektrochemischen Detektion der Katecholamine in Plasma- und Urinproben" (Optimization of the Signal-to-Noise Ratio in the Electrochemical Detection of Catecholamines in Plasma and Urine Samples) by W. Bauersfeld and H. Wissner, published in the collection "Konigsteiner Chromatographietage, Oct. 4 to 6, 1982, Travemunde/Ostsee" (seminar of the firm Waters), to accommodate the detector cell in a Faraday cage on the one hand, and on the other hand to use an additional filter for the detector electronics for the purpose of reducing the noise component of the chromatogram. In this manner, it was possible to achieve a reduction of the noise down to a peak-to-peak value of 2 $pA_{ss}$, which according to that article was not attained before. This value is shown in the chromatogram in FIG. 2 which is taken from the afore-mentioned publication.

It is thus desirable to provide a method and an apparatus for electrochemical detection by means of which the noise component in the chromatogram can be reduced considerably and the analysis sensitivity can thus be increased.

SUMMARY OF THE INVENTION

The invention is based on the realization that an electrochemical detector of the type described is subjected to complex interference influences which are in particular ground loop problems, but also interference field irradiations and electrostatic fields having a capacitive influence. Ground loop problems are caused in that various components of the chromatographic system may have different ground potentials since the ground conductors connected to the ground terminals of these components may have different potentials, for instance due to thermoelectric phenomena at plug connectors, line terminals etc. Due to the fact that the electrolytic solution flowing through the chromatographic system acts as an electrical conductor itself, interference voltages occur in the measuring system which result in an interfering influence of the difference between the potential of the working electrode and the potential of the electrolyte in the region of the working electrode.

According to the present invention, the potential applied to the electrolyte via the auxiliary electrode is not adjusted any more to provide the desired potential difference with respect to the working electrode, as was done before, but rather, the instantaneous electric potential value of the electrolyte in the local region of the working electrode is simply measured and the working electrode potential is controlled as a function of the measured instantaneous potential value.

It is advantageous to have the potential of the working electrode follow-up a varying electrolyte potential rather than to suppress potential variations of the electrolyte by means of a control process. This is achieved preferably in that a potential corresponding to the potential difference required for the electrolysis is superimposed on the measured instantaneous potential value and in that the resulting potential is impressed on the working electrode.

This can be achieved in a relatively simple manner by connecting the output of the measuring electrode to an input of a summing circuit which is connected to an electrolysis potential difference source via a second input, the output of the summing circuit being connected to the working electrode, preferably via a current measuring means.

A particularly preferred embodiment includes a current-voltage converter by means of which the measurement signal current collected from the working electrode is converted into a measurement signal voltage which then is applied to the input of a chromatogram recorder. Preferably, an operational amplifier designed as differential amplifier is used as a current-voltage converter, to the non-inverting input of which operational amplifier the output signal of the summing circuit is supplied and the inverting input of which is connected to the working electrode and the output of which is connected to the inverting input via a feedback resistor. The output signal of this differential amplifier is applied to the input of the chromatogram recorder after appropriate further processing thereof.

The technical expenditure is particularly low when this operational amplifier is attributed a double function, namely on the one hand the function of a currentvoltage converter and on the other hand the function of the summing circuit. For this purpose, the differential amplifier serving as operational amplifier is selected or designed such that it has an offset voltage corresponding to the potential difference between the working electrode and the electrolyte, required for the electrolysis. As regards electrochemical detectors which are fixedly designed for the analysis of certain substances, this offset voltage may represent a constant fixed value. However, when the electrochemical detector is intended for varied use for the analysis of various substances or groups of substances, it is advantageously provided with a means for adjusting the particular desired offset voltage in accordance with the particular required potential difference between the working electrode and the electrolyte.

For the purpose of maintaining the electrolyte in the total detector arrangement at a potential as constant as possible on the one hand and in order to avert on the other hand influences of noise fields and electrostatic fields, the detector cell is, in a particularly preferred manner, designed with a metallic housing block accommodating the inlet and the outlet, and the inlet line up to the solution source. Preferably the pump and also the outlet line are formed of metal. In order to obtain a flexibility of the lines, they may be made of plastic tubes which are coated with metal on the outside or on the inside or which are covered with a metallic shielding braid. Preferably, the same metal as that used for the housing block is used for the inlet line and for the outlet line in order to avoid potential transitions between the housing block and these lines. This measure for averting interference influences may be taken in connection with as well as independently of the aforementioned electrical circuit measures.

It is particularly preferred to form the detector cell completely of metal, with the working electrode and the measuring electrode each being embedded in insulated manner in the housing part receiving them, the measuring electrode being embedded in this manner by way of the insulating jacket belonging to it. The working electrode and preferably also the measuring electrode, inclusive of the respective lead, is provided with a shielding. Then, it is not necessary any more to accommodate the measuring arrangement in a Faraday cage which is space-consuming and renders the access to the measuring arrangement more difficult. This feature according to the invention can be used together with the electrical circuit features and/or together with the metallic inlet and outlet lines, or it can be used independently thereof.

When using a measuring electrode which is not current-resistant, the counter-electrode arrangement consists of the measuring electrode and of the auxiliary electrode. When using a measuring electrode which is current-resistant, the counter-electrode arrangement may consist exclusively of the measuring electrode and the auxiliary electrode can be dispensed with.

BRIEF DESCRIPTION OF THE DRAWINGS

The invention will now be described in more detail by way of specific embodiments and with reference to the accompanying drawings in which.

DETAILED DESCRIPTION

Figure 1:
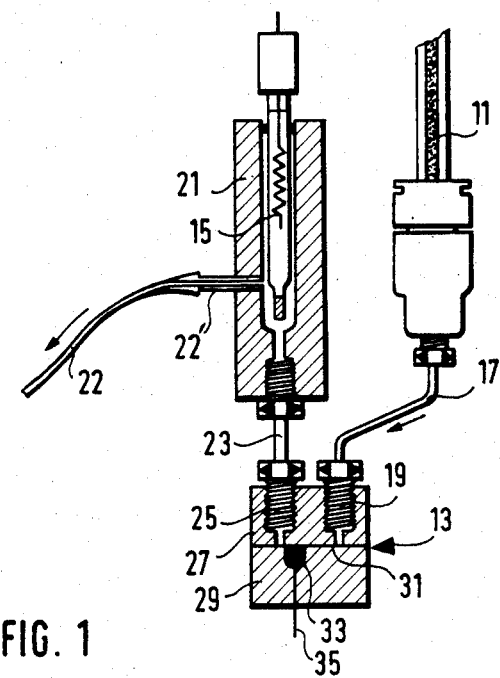
FIG. 1 shows the aforementioned conventional electrochemical detector.

The conventional electrochemical detector shown in FIG. 1 comprises a detector cell 13 and a measuring electrode 15. An analytical column 11 is connected to an inlet 19 of the detector cell 13 by means of an inlet line 17 of plastic material. The measuring electrode 15 is accommodated in a measuring electrode housing 21 to which an outlet 25 of the detector cell 13 is connected via an outlet line 23 made of plastic material. The measuring electrode housing 21 has an outlet line 22, a short piece 22' of which is designed as metal tube which serves as an auxiliary electrode.

The detector cell 13 consists of two housing parts 27 and 29 of plastic material between which a solution flow space 31 is formed. The inlet 19 and the outlet 25, which are formed in the upper housing part 27, open into said solution flow space 31 while being spaced apart from each other.

Embedded in lower housing part 29 is a working electrode 33 which extends into the solution flow space 31 and is in electrical contact with the electrolytic solution flowing through the solution flow space 31. The solution flow space 31 is designed such that the electrolytic solution flowing therethrough adopts the shape of a thin-layer. An electrical lead 35 is connected to the working electrode 33.

In operation, the working electrode is maintained at ground potential, and a potential is impressed on the electrolytic solution by means of the auxiliary electrode 22', so that the electrolytic solution displays the potential difference with respect to the potential of the working electrode, which is necessary for the electrochemical detection. The potential of the electrolyte is measured by means of the measuring electrode 21 and controlled to have the nominal value by means of the auxiliary electrode 22'.

The current present at the working electrode 33 is applied to the input of a chromatogram recorder after it has been subjected to signal processing, especially a current-voltage conversion, a variable amplification and a filtering step.

The electrolytic solution may be subjected to numerous disturbances on its way from the column 11 to the auxiliary electrode 22'. The column 11 and the pump arranged upstream thereof usually have a metal housing. The housings thereof are grounded for safety reasons. Due to the problems mentioned hereinbefore, the ground potentials of the pump, the column 11 and the working electrode 33 may differ. Thus, the electrolytic solution acting as an electrical conductor is subjected to a mixture of potentials. Due to this the potential of the electrolyte in the region of the working electrode 33 can differ from the potential of the electrolyte in the region of the measuring electrode 15. This in turn can differ from the potential of the electrolyte in the region of the auxiliary electrode 22'. Thus, fluctuations of the electrolyte potential at the location of the measuring electrode 15 may be different from the fluctuations of the electrolyte potential at the location of the working electrode 33. As a result the electrolyte has a different potential in the region of the working electrode 33 than in the region of the measuring electrode 15. The potential of electrode 15 is controlled by means of the auxiliary electrode 22'. This causes interference in the basic signal of the chromatogram.

Furthermore, high frequency fields and electrostatic fields created by charged objects or persons may act on the electrolytic solution while it flows from the column 11 through the plastic inlet line 17, the plastic housing of the detector 13 and the plastic outlet line 23 to the measuring electrode 15 and from there onwards to the auxiliary electrode 22'. The latter disturbances necessitate that conventional electrochemical detectors must be operated in Faraday cages.

Figure 2:
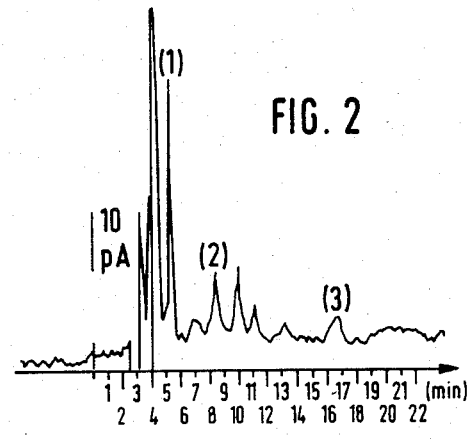
FIG. 2 shows the aforementioned chromatogram obtained by using a conventional electrochemical detector.

FIG. 2 shows the aforementioned chromatogram obtained by using a conventional electrochemical detector apparatus. This chromatogram shows three peaks distributed over the time axis, with peak (1) being caused by 22 noradrenaline, peak (2) by 7 adrenaline and peak (3) by 5 dopamine. With the aid of the ordinate scale of 10 pA/inserted length unit drawn into the chromatogram it is recognizable that a noise and interference signal having a peak-to-peak value of about 2 $pA_{pp}$ is superimposed on the basic signal value of this chromatogram.

Figure 3:
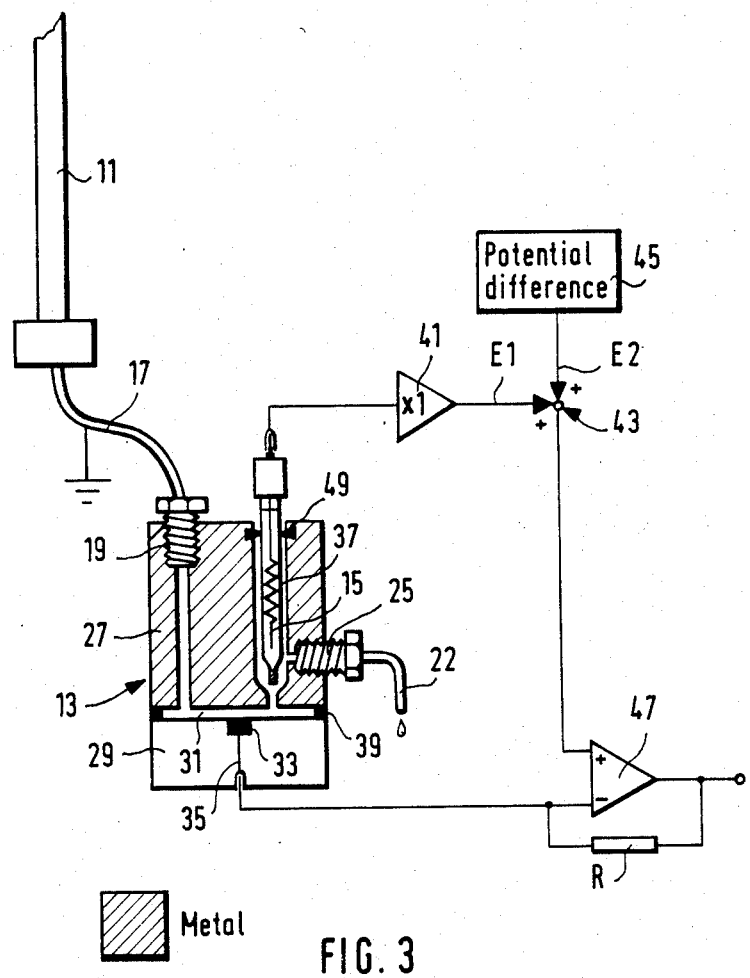
FIG. 3 shows an embodiment of an apparatus for electrochemical detection according to the present invention.

A first embodiment of an apparatus for electrochemical detection according to the present invention is shown in FIG. 3, in which components corresponding to components shown in FIG. 1 have the same reference numerals. The mode of operation is the same as with the electrochemical detector in FIG. 1, unless stated otherwise hereinafter.

The electrochemical detector shown in FIG. 3 comprises a detector cell 13. The upper (as shown in the drawing) housing part 27 consists of a metal block. The inlet 19 as well as the outlet 25 open into the metal block. Furthermore, the metal block 27 comprises a measuring electrode opening 37 into which the measuring electrode 15 is inserted such that its measuring end is located near the solution flow space 31. The inlet line 17 and the outlet line 22 both consist of metal tubes. Preferably, the same material is used for these metal tubes as for the metal block 27 in order to avoid potential transitions at the material transitions between the metal tubes and the metal block.

The lower housing part 29 (i.e. lower with respect to FIG. 3) consists of a plastic block which, by means of a gasket 39 acting as spacer, is held at a distance from the metallic upper housing part 27 in order to form the solution flow space 31 between these two housing parts 27 and 29.

A very important aspect of the invention is that the auxiliary electrode, which is formed by the metallic inlet line 17 and the metal parts of the arrangement connected thereto, is not used for controlling the electrolyte to a potential difference with respect to the working electrode 33, but that the auxiliary electrode is fixed at ground potential. The potential of the electrolyte near the working electrode 33 is measured by means of the measuring electrode 15, and the measured value is applied to a first input E1 of a summing circuit 43 via an impedance transformer 41. The particular instantaneous potential value of the electrolyte at the location of the measuring electrode 15 is available at this input E1. A second input E2 of the addition circuit 43 is connected to the output of a potential difference source 45. The potential difference source 45 provides a voltage which corresponds to the desired difference between the potential of the electrolyte in the region of the working electrode 33 and the potential of the working electrode 33 itself. Thus, the output of the summing circuit 43 always is controlled to have a voltage value which is higher or lower by the potential difference than the particular instantaneous value of the electrolyte potential in the region of the working electrode 33.

The output of the summing circuit 43 is connected to the non-inverting input of an operational amplifier 47 the inverting input of which is connected to the lead 35 of the working electrode 33. The output of the operational amplifier 47 is fed back to its inverting input via a resistor R. Due to the known behavior of an operational amplifier which is fed back in such a manner, the potential present at its non-inverting input is the same as the potential present at its inverting input. Thus, the potential occurring at the output of the summing circuit 43 is also present at the working electrode 33. Consequently, the potential of the working electrode 33 is at any time controlled to have a value which is higher or lower by the potential difference from the potential difference source 45 than the instantaneous potential value of the electrolyte in the local region of the working electrode 33. Fluctuations of the absolute value of the electrolyte potential cannot have a detrimental effect any more, since the absolute value of the potential of the working electrode 33 is controlled in a correspondingly fluctuating manner, i.e. since the potential difference between the electrolyte potential and the working electrode potential is maintained at a constant value.

At the working electrode 33, there occurs an electrical current which depends on the particular instantaneous electrolyzing capability of the electrolytic solution flowing past the working electrode 33. With the aid of the operational amplifier 47 serving as currentvoltage converter, the current supplied from the working electrode 33 is converted into a corresponding voltage which is available at the output of the operational amplifier 47. This output voltage of the operational amplifier 47, after appropriate processing thereof, especially a further amplification, potential shifting and filtering, is applied to the input of a chromatogram recorder.

Due to the fact that the inlet line 17, the outlet line 22 and the housing part 27 containing the inlet 19, the inlet 25 and the measuring electrode 15 consist of metal, the electrolytic solution is not only maintained at virtually the same potential on its whole flow path from the exit of the column 11 to the exit of the outlet line 22, but an effective shielding with respect to high frequency fields and electrostatic fields is achieved as well.

According to a particularly advantageous further development of the invention it is also possible to make the lower housing part 29 (in FIG. 3) of metal, and preferably of the same metal of which the upper housing part 29 consists. The working electrode 33 and the lead 35 thereof will then be held in the lower metal housing block in an electrically insulated manner. Preferably, the working electrode 33 as well as the measuring electrode 15, each together with the lead, will be provided with a shielding. For example, the lead 35 of the working electrode 33 will be designed as shielded cable and the shielding of the cable will be connected to the metallic housing part 29. In this embodiment of the invention a shielding Faraday cage can be dispensed with completely.

For the purpose of keeping the shielding as perfect as possible, the metallic inlet line 17 is preferably placed as far as possible into the metal housing of the column 11. If the column 11 and/or the pump arranged upstream of the column 11 has an electrolyte line of insulating material in its metal housing, an electrical connection will be established advantageously between the metallic inlet line 17 and the metal housing of the column 11 and, if applicable, the pump.

The measuring electrode is usually arranged in an insulating jacket which ends with an ion-permeable membrane at the measuring end of the measuring electrode. Therefore, it is only necessary to provide an opening 37 for the measuring electrode arrangement in the metallic housing part 27 and to provide a seal 49 between the measuring electrode arrangement and the measuring electrode opening.

In the electrochemical detector shown in FIG. 3, there are equipotential surfaces in the electrolyte flowing through the solution flow space 31 when there is a current flow in the working electrode, and these equipotential surfaces run approximately parallel to the upper and lower confirming areas of the solution flow space 31. The electrolyte adjacent the working electrode 33, thus, is at a different potential than the electrolyte present at the measuring electrode 15.

Figure 4:
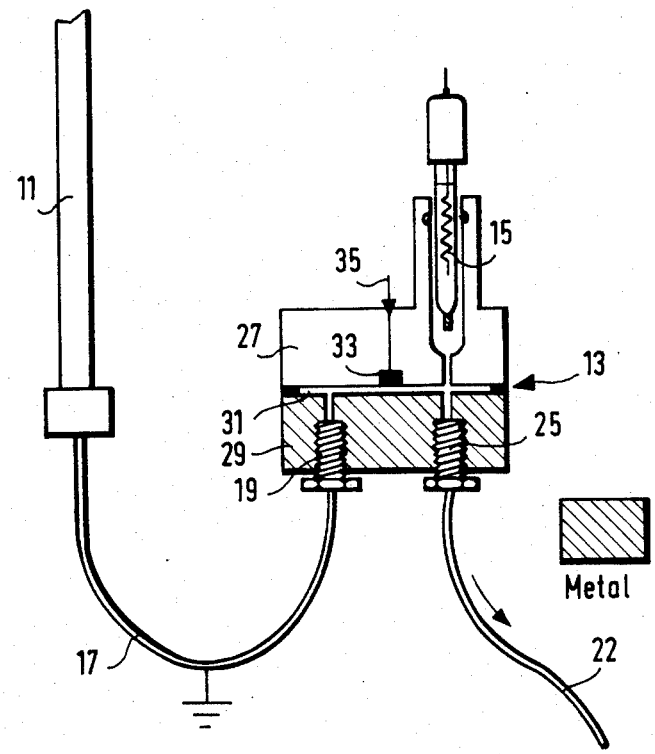
FIG. 4 shows an embodiment of an electrochemical detector according to the present invention, having a modified detector cell.

FIG. 4 shows an embodiment of the electrochemical detector according to the invention in which the working electrode 33 and a connection to the measuring electrode 15 are both accommodated in the upper housing part 27, and the inlet 19 and the outlet 25 are accommodated in the lower housing part 29. The electrolyte present in the region of the working electrode 33 and the electrolyte present in the region of the lead to the measuring electrode 15 are located practically on the same equipotential surface in this embodiment, so that this embodiment is still improved in comparison with the embodiment illustrated in FIG. 3.

As for the rest, there is substantial correspondence with the embodiment according to FIG. 3. In this case too, the working electrode 33 is connected to the inverting input of the operational amplifier 47 and the measuring electrode 15 is connected to the impedance transformer 41.

Figure 5:
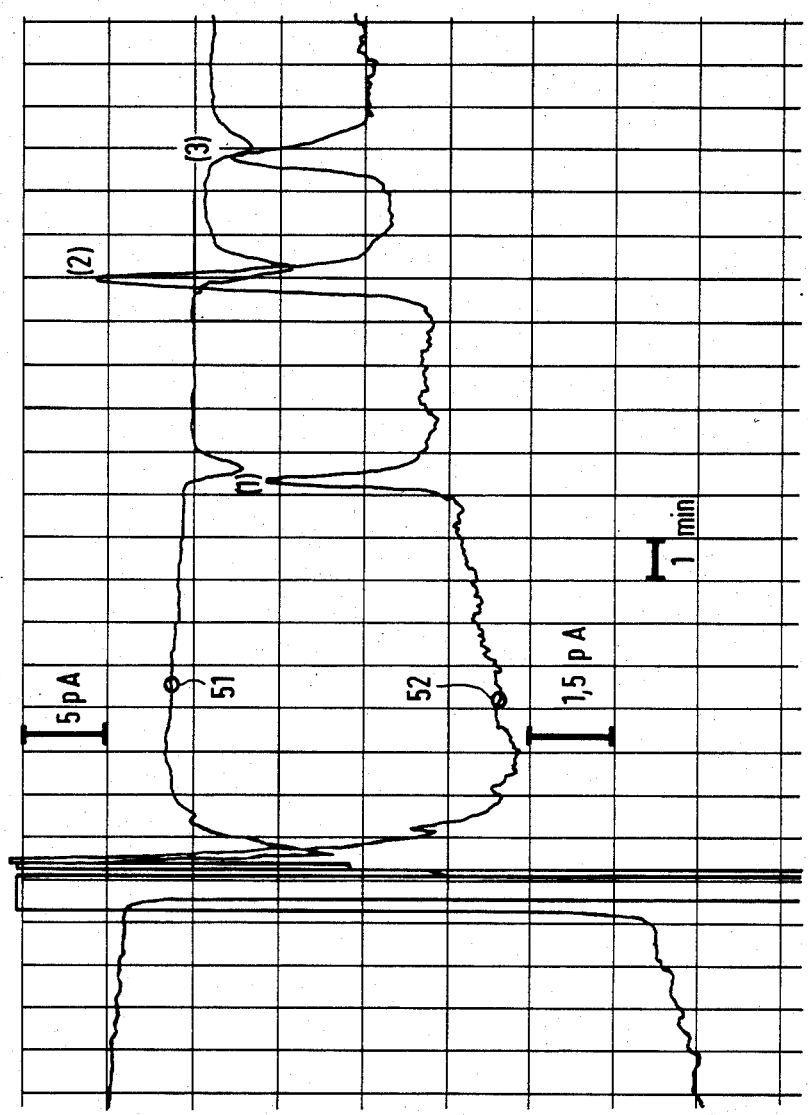
FIG. 5 shows a chromatogram obtained by using the apparatus for electrochemical detection according to the present invention.

FIG. 5 shows a chromatogram recorded with the aid of the method according to the present invention and with the aid of an apparatus for electrochemical detection according to the present invention. This chromatogram shows two measuring curves 51 and 52 which are both based on the same measurement signal but which have been produced by using a different recording sensitivity. The scales of sensitivity are shown above and below the measuring curves 51 and 52, respectively.

The curves 51 and 52 each show a peak (1) which is based on 2.3 pg noradrealine, a peak (2) which is caused by 5.2 pg dihydroxybenzylamine and a peak (3) which is based on 3.46 pg adrenaline. Although the concentrations are much lower than in the chromatogram according to FIG. 2, these peaks rise much more above the background noise than in FIG. 2.

A comparison of the lower curve 52 with the sensitivity scale indicated for this curve shows that the interference and noise components superimposed on the basic signal of this chromatogram have peak-to-peak values of about 0.2 to 0.3 $pA_{pp}$. This is an improvement by a factor of more than 6 in comparison with the chromatogram shown in FIG. 2, which was recorded by means of a conventional method and a conventional apparatus for electrochemical detection. Therefore, considerably lower concentrations than possible heretofore with the conventional apparatus shown can be analyzed by means of the method according to the present invention and the detector apparatus according to the present invention.

It is apparent to one skilled in the art having the benefit of this disclosure that there has been provided in accordance with this invention a method and an apparatus for electrochemical detection which address the objects, means and advantages set forth hereinbefore. While the invention has been described with the specific embodiments thereof, it is evident that many alternatives, modifications and variations will be apparent to those skilled in the art in the light of the foregoing description. Accordingly, it is intended to embrace all such alternatives, modifications and variations as fall within the spirit and broad scope of the appended claims.

What is claimed is:

1. An electrochemical detector comprising:
    a detector cell having a housing with a solution flow space and a metallic housing block accommodating an inlet and an outlet for an electrolytic solution to be analyzed, the inlet being connected to a solution source via an inlet line comprising a metallic inlet line up to the solution source and the outlet being connected to a discharge means via an outlet line;

a working electrode extending into the solution flow space of the housing and in contact with a solution flowing through the solution flow space;

a counter-electrode arrangement configured such that by means of the counter-electrode arrangement an electrical potential can be impressed on the solution;

an electrical adjustment circuit for maintaining a substantially constant potential difference between the working electrode and the electrolyte; and an electrical measuring circuit for measuring the electrolysis current generated at the working electrode.

2. An electrochemical detector according to claim 1, wherein the outlet line comprises a metallic outlet line.

3. An electrochemical detector according to claim 2, wherein the inlet line and the outlet line comprise the same metal as that used for the housing block.

4. An electrochemical detector according to claim 2 wherein the metallic housing block with the metallic inlet line and the metallic outlet line serves as an auxiliary electrode by means of which a reference potential is applied to the electrolytic solution.

5. An electrochemical detector according to claim 1 wherein the solution source comprises a metallic body in contact with the electrolytic solution and wherein the metallic inlet line is electrically connected to the metallic body.

6. An electrochemical detector according to claim 1, wherein the solution source has a metallic housing, and wherein the metallic inlet line is electrically connected to the metallic housing.

7. An electrochemical detector according to claim 1 wherein the solution flow space is provided with an inlet and an outlet and is confined by two housing parts adjacent the solution flow space, and the working electrode extends through one housing part and into the solution flow space, with the inlet, the outlet and an opening for the measuring electrode being formed in the other housing part made of a one-piece metal block.

8. An electrochemical detector according to claim 7, wherein both housing parts comprise the same metal, with the working electrode being embedded in an insulated manner in the housing part accommodating said working electrode.

9. An electrochemical detector according to claim 1, comprising a detector cell wherein the solution flow space is confined by first and second housing parts adjacent the solution flow space, with the inlet and the outlet for the solution flow space being formed in the first housing part and openings for the measuring electrode and the working electrode being formed in the second housing part and wherein said first housing part is formed of a one-piece metal block.

10. An electrochemical detector according to claim 9, wherein both housing parts consist of the same metal, with the working electrode being embedded in an insulated manner in the housing part accommodating said working electrode.

11. An electrochemical detector comprising:
a detector cell having an inlet and an outlet for an electrolytic solution to be analyzed;

a housing comprising a metallic housing block accommodating the inlet and the outlet;

an inlet line connected to the inlet and comprising a metallic inlet up to a solution source;

a working electrode which is in contact with the solution flowing through a solution flow space;

a counter-electrode arrangement by means of which an electrical reference potential can be impressed on the solution;

an electrical potential measuring electrode adapted to measure the instantaneous potential value of the solution in the region of the working electrode, the electrical potential measuring electrode being connected to a first input of a summing circuit which has a second input connected to the output of an electrolysis potential difference source, and the output of which is connected to the working electrode, the electrolysis potential difference source being adapted to supply an electrical potential capable of effecting the electrolysis of the substance to be analyzed in the solution flowing past the working electrode; and an electrical measuring circuit for measuring the electrolysis current generated at the working electrode.

12. An electrochemical detector according to claim 11, wherein the solution source has a metallic housing, and wherein the metallic inlet line is electrically connected to the metallic housing.

13. An electrochemical detector according to claim 11, wherein the solution flow space is provided with an inlet and an outlet and is confined by two housing parts adjacent the solution flow space, and the working electrode extends through one housing part and into the solution flow space, with the inlet, the outlet and an opening for the measuring electrode being formed in the other housing part made of a one-piece metal block.

14. An electrochemical detector according to claim 13, wherein both housing parts comprise the same metal, with the working electrode being embedded in an insulated manner in the housing part accommodating said working electrode.

15. An electrochemical detector according to claim 11, comprising a detector cell wherein the solution flow space is confined by first and second housing parts adjacent the solution flow space, with the inlet and the outlet for the solution flow space being formed in the first housing part and openings for the measuring electrode and the working electrode being formed in the second housing part and wherein said first housing part is formed of a one-piece metal block.

16. An electrochemical detector according to claim 15, wherein both housing parts consist of the same metal, with the working electrode being embedded in an insulated manner in the housing part accommodating said working electrode.

17. An electrochemical detector according to claim 11, wherein the outlet line comprises a metallic outlet line.

18. An electrochemical detector according to claim 17, wherein the inlet line and the outlet line comprise the same metal as that used for the housing block.

19. Apparatus for detecting a substance in a liquid electrolyte, which comprises:
a cell defining a flow path for the flow of said electrolyte through the cell;
a working electrode positioned within said flow path;

a potential detector to detect the instantaneous electrical potential of said electrolyte in said flow path;

a source of electrical potential to provide an electrical potential capable of electrolyzing said substance in said electrolyte;

a summing circuit to sum said instantaneous electrical potential detected by said potential detector with said electrical potential;

circuit means to apply the resulting summed potential to said working electrode; and detector means to detect current generated at said working electrode.

20. An electrochemical detector according to claim 19, wherein said summing circuit is formed by a differential amplifier, a non-inverting input of which is connected to the potential detector and an inverting input of which is connected to the working electrode on the one hand, and on the other hand to an output of the differential amplifier via a feedback resistor, and on the output of which can be taken off a detection signal as an analysis measurement signal and wherein the differential amplifier is designed for effecting an offset voltage in accordance with a potential difference between the working electrode and the electrolyte required for the electrolysis.

21. An electrochemical detector according to claim 19 wherein an impedance transformer is interconnected between said potential detector and said summing circuit.

22. An electrochemical detector according to claim 19 wherein said potential detector comprises a measuring electrode connected to a first input of said summing circuit.

23. The apparatus of claim 19, including an auxiliary electrode to apply a reference potential to said electrolyte in said cell.

24. The apparatus of claim 19 or 23, including an operational amplifier having an inverting input connected to said working electrode, a non-inverting input adapted to receive said summed potentials, and a feedback connection to feed the output of said amplifier to said inverting input.

25. A method for detecting the presence of a substance in an electrolytic solution, comprising the steps of:

detecting the instantaneous electrical potential of said solution;

summing the detected potential with a second potential capable of electrolyzing said substance in said solution;

impressing the resulting summed potential on an electrode for electrolyzing said substance; and detecting the current flow resulting from such electrolysis.

26. The method of claim 25 in which a reference potential is imposed on said solution.

27. The method of claim 25 or 26 which includes the step of converting the detected current flow into a measurement signal voltage.

* * * * *